United States Patent
Li et al.

(10) Patent No.: US 9,938,284 B2
(45) Date of Patent: Apr. 10, 2018

(54) ORGANIC COMPOUNDS

(71) Applicant: INTRA-CELLULAR THERAPIES, INC., New York, NY (US)

(72) Inventors: Peng Li, New Milford, NJ (US); Hailin Zheng, Teaneck, NJ (US); Jun Zhao, Highland Park, NJ (US); Lawrence P. Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 15/502,455

(22) PCT Filed: Aug. 6, 2015

(86) PCT No.: PCT/US2015/044051
§ 371 (c)(1),
(2) Date: Feb. 7, 2017

(87) PCT Pub. No.: WO2016/022825
PCT Pub. Date: Feb. 11, 2016

(65) Prior Publication Data
US 2017/0217975 A1 Aug. 3, 2017

Related U.S. Application Data

(60) Provisional application No. 62/034,593, filed on Aug. 7, 2014.

(51) Int. Cl.
*C07D 487/14* (2006.01)

(52) U.S. Cl.
CPC .................................. *C07D 487/14* (2013.01)

(58) Field of Classification Search
CPC .................................................... C07D 487/04
See application file for complete search history.

(56) References Cited

U.S. PATENT DOCUMENTS

| | | | |
|---|---|---|---|
| 4,238,616 A | 12/1980 | Nadelson | |
| 7,053,219 B2 * | 5/2006 | Nakamura | C07D 498/04 546/115 |
| 8,273,750 B2 | 9/2012 | Li et al. | |
| 2004/0087653 A1 | 5/2004 | Manning | |
| 2006/0083714 A1 | 4/2006 | Warner | |
| 2008/0188492 A1 | 8/2008 | Li et al. | |

FOREIGN PATENT DOCUMENTS

| | | |
|---|---|---|
| CA | 2296224 A1 | 1/2000 |
| WO | WO 2006/133261 A2 | 12/2006 |
| WO | WO 2009/075784 A1 | 6/2009 |

OTHER PUBLICATIONS

Bender, A., et al., "Selective Up-regulation of PDE1B2 upon Monocyte-to-Macrophage Differentiation," PNAS, 2005, vol. 102, No. 2, pp. 497-502.
Evgenov, O., et al., "Inhibition of Phosphodiesterase 1 Augments the Pulmonary Vasodilator Response to Inhaled Nitric Oxide in Awake Lambs with Acute Pulmonary Hypertension," Am. J. Physiol. Lung Cell Mol. Physiol., 2006, vol. 290, pp. L723-L729.
Kakkar, R., et al., "Calmodulin-dependent Cyclic Nucleotide Phosphodiesterase in an Experimental Rat Model of Cardiac Ischemia-reperfusion," Can. J. Physiol. Pharmacol., vol. 80, No. 1, pp. 59-66, Abstract only.
Kim, D., et al., "Upregulation of Phosphodiesterase 1A1 Expression Is Associated With the Development of Nitrate Tolerance," Circulation, 2001, vol. 104, pp. 2338-2343, doi: 10.1161/hc4401.098432, accessed on Jul. 20, 2016.
Miller, C.L., "Role of $Ca^{2+}$/Calmodulin-Stimulated Cyclic Nucleotide Phosphodiesterase 1 in Mediating Cardiomyocyte Hypertrophy," Circulation Research, 2009, vol. 105, pp. 956-964, doi: 10.1161/CIRCRESAHA.109.198515, accessed on Jul. 21, 2016.
Mokni, W., et al., "Concerted Regulation of cGMP and cAMP Phosphodiesterases in Early Cardiac Hypertrophy Induced by Angiotensin II," PLoS ONE, 2010, vol. 5, No. 12, pp. e14227.
Rybalkin, S., et al., "Cyclic Nucleotide Phosphodiesterase 1C Promotes Human Arterial Smooth Muscle Cell Proliferation," Circulation Research, 2002, vol. 90, pp. 151-157, doi: 10.1161/hh0202.104108, accessed Jul. 20, 2016.
Shermuly, R., et al., "Phosphodiesterase 1 Upregulation in Pulmonary Arterial Hypertension: Target for Reverse-Remodeling Therapy," Circulation, 2007, vol. 115, pp. 2331-2339, doi: 10.1161/CIRCULATIONAHA.106.676809, accessed on Jul. 21, 2016.
Takimoto, E., "Controlling Myocyte cGMP: Phosphodiesterase 1 Joins the Fray," Circulation Research, 2009, vol. 105, pp. 931-933, http://circres.ahajournals.org, doi: 10.1161/CIRCRESAHA.109.209700, accessed on Nov. 2, 2017.
Willerson, J., et al., "Inflammation as a Cardiovascular Risk Factor," Circulation, 2004, vol. 109, Suppl. II, pp. II-2-II-10, doi: 10.1161/01.CIR.0000129535.04194.38, accessed on Jul. 21, 2016.

* cited by examiner

*Primary Examiner* — Erich A Leeser
(74) *Attorney, Agent, or Firm* — Hoxie & Associates LLC

(57) ABSTRACT

The invention relates to novel inhibitors of phosphodiesterase 1 (PDE1), useful for the treatment of diseases or disorders characterized by disruption of or damage to certain cGMP/PKG mediated pathways (e.g., in cardiac tissue). The invention further relates to pharmaceutical composition comprising the same and methods of treatment of cardiovascular disease and related disorders, e.g., congestive heart disease, atherosclerosis, myocardial infarction, and stroke.

30 Claims, No Drawings

ORGANIC COMPOUNDS

CROSS REFERENCE TO RELATED APPLICATIONS

This application is a United States Application under 35 U.S.C. § 371 claiming benefit of PCT Application No. PCT/US2015/044051, filed on Aug. 6, 2015, which claims priority to and the benefit of U.S. Provisional Application No. 62/034,593, filed on Aug. 7, 2014, the contents of each of which are hereby incorporated by reference in their entireties.

FIELD OF THE INVENTION

The invention relates to novel inhibitors of phosphodiesterase 1 (PDE1) useful for the treatment of diseases or disorders characterized by disruption of or damage to certain cGMP/PKG mediated pathways (e.g., in cardiac tissue or in vascular smooth muscle). The invention further relates to pharmaceutical composition comprising the same and methods of treatment of cardiovascular disease and related disorders, e.g., congestive heart disease, atherosclerosis, myocardial infarction, and stroke.

BACKGROUND OF THE INVENTION

Heart disease is a chronic and progressive illness that kills more than 2.4 million Americans each year. There are approximately 500,000 new cases of heart failure per year, with an estimated 5 million patients in the United States alone having this disease. Early intervention is likely to be most effective in preserving cardiac function. It would be most desirable to prevent as well to reverse the morphological, cellular, and molecular remodeling that is associated with heart disease. Some of the most important indicators of cardiac risk are age, hereditary factors, weight, smoking, blood pressure, exercise history, and diabetes. Other indicators of cardiac risk include the subject's lipid profile, which is typically assayed using a blood test, or any other biomarker associated with heart disease or hypertension. Other methods for assaying cardiac risk include, but are not limited to, an EKG stress test, thallium stress test, EKG, computed tomography scan, echocardiogram, magnetic resonance imaging study, non-invasive and invasive arteriogram, and cardiac catheterization.

Pulmonary hypertension (PH or PHT) is an increase in blood pressure in the pulmonary artery, pulmonary vein, and/or pulmonary capillaries. It is a very serious condition, potentially leading to shortness of breath, dizziness, fainting, decreased exercise tolerance, heart failure, pulmonary edema, and death. It can be one of five different groups, classified by the World Health Organization in categories described below.

WHO Group I—Pulmonary arterial hypertension (PAH):
  a. Idiopathic (IPAH)
  b. Familial (FPAH)
  c. Associated with other diseases (APAH): collagen vascular disease (e.g. scleroderma), congenital shunts between the systemic and pulmonary circulation, portal hypertension, HIV infection, drugs, toxins, or other diseases or disorder.
  d. Associated with venous or capillary disease.

Pulmonary arterial hypertension involves the vasoconstriction or tightening of blood vessels connected to and within the lungs. This makes it harder for the heart to pump blood through the lungs, much as it is harder to make water flow through a narrow pipe as opposed to a wide one. Over time, the affected blood vessels become both stiffer and thicker, in a process known as fibrosis. This further increases the blood pressure within the lungs and impairs their blood flow. In addition, the increased workload of the heart causes thickening and enlargement of the right ventricle, making the heart less able to pump blood through the lungs, causing right heart failure. As the blood flowing through the lungs decreases, the left side of the heart receives less blood. This blood may also carry less oxygen than normal. Therefore, it becomes more and more difficult for the left side of the heart to pump to supply sufficient oxygen to the rest of the body, especially during physical activity.

WHO Group II—Pulmonary hypertension associated with left heart disease:
  a. Atrial or ventricular disease
  b. Valvular disease (e.g. mitral stenosis)

In pulmonary hypertension WHO Group II, there may not be any obstruction to blood flow in the lungs. Instead, the left heart fails to pump blood efficiently out of the heart into the body, leading to pooling of blood in veins leading from the lungs to the left heart (congestive heart failure or CHF). This causes pulmonary edema and pleural effusions. The fluid build-up and damage to the lungs may also lead to hypoxia and consequent vasoconstriction of the pulmonary arteries, so that the pathology may come to resemble that of Group I or III.

WHO Group III—Pulmonary hypertension associated with lung diseases and/or hypoxemia:
  a. Chronic obstructive pulmonary disease (COPD), interstitial lung disease (ILD)
  b. Sleep-disordered breathing, alveolar hypoventilation
  c. Chronic exposure to high altitude
  d. Developmental lung abnormalities In hypoxic pulmonary hypertension (WHO Group III), the low levels of oxygen may cause vasoconstriction or tightening of pulmonary arteries. This leads to a similar pathophysiology as pulmonary arterial hypertension.

WHO Group IV—Pulmonary hypertension due to chronic thrombotic and/or embolic disease:
  a. Pulmonary embolism in the proximal or distal pulmonary arteries
  b. Embolization of other matter, such as tumor cells or parasites In chronic thromboembolic pulmonary hypertension (WHO Group IV), the blood vessels are blocked or narrowed with blood clots. Again, this leads to a similar pathophysiology as pulmonary arterial hypertension.

WHO Group V—Miscellaneous

Treatment of pulmonary hypertension has proven very difficult. Antihypertensive drugs that work by dilating the peripheral arteries are frequently ineffective on the pulmonary vasculature. For example, calcium channel blockers are effective in only about 5% of patients with IPAH. Left ventricular function can often be improved by the use of diuretics, beta blockers, ACE inhibitors, etc., or by repair/replacement of the mitral valve or aortic valve. Where there is pulmonary arterial hypertension, treatment is more challenging, and may include lifestyle changes, digoxin, diuretics, oral anticoagulants, and oxygen therapy are conventional, but not highly effective. Newer drugs targeting the pulmonary arteries, include endothelin receptor antagonists (e.g., bosentan, sitaxentan, ambrisentan), phosphodiesterase type 5 inhibitors (e.g., sildenafil, tadalafil), prostacyclin derivatives (e.g., epoprostenol, treprostenil, iloprost, beroprost), and soluble guanylate cyclase (sGC) activators (e.g., cinaciguat and riociguat). Surgical approaches to PAH include atrial septostomy to create a communication between the right and left atria, thereby relieving pressure on the right side of the heart, but at the cost of lower oxygen levels in blood (hypoxia); lung transplantation; and pulmonary thromboendarterectomy (PTE) to remove large clots along with the lining of the pulmonary artery. Heart failure and acute myocardial infarction are common and serious conditions frequently associated with thrombosis and/or plaque build-up in the coronary arteries.

Cardiovascular disease or dysfunction may also be associated with diseases or disorders typically thought of as affecting skeletal muscle. One such disease is Duchenne muscular dystrophy (DMD), which is a disorder that primarily affects skeletal muscle development but can also result in cardiac dysfunction and cardiomyopathy. DMD is a recessive X-linked form of muscular dystrophy, affecting around 1 in 3,600 boys, which results in muscle degeneration and eventual death. The disorder is caused by a mutation in the dystrophin gene, located on the human X chromosome, which codes for the protein dystrophin, an important structural component within muscle tissue that provides structural stability to the dystroglycan complex (DGC) of the cell membrane. While both sexes can carry the mutation, females rarely exhibit signs of the disease.

Patients with DMD either lack expression of the protein dystrophin or express inappropriately spliced dystrophin, as a result of mutations in the X-linked dystrophin gene. Additionally, the loss of dystrophin leads to severe skeletal muscle pathologies as well as cardiomyopathy, which manifests as congestive heart failure and arrhythmias. The absence of a functional dystrophin protein is believed to lead to reduced expression and mis-localization of dystrophin-associated proteins including Neuronal Nitric Oxide (NO) Synthase (nNOS). Disruption of nNOS signaling may result in muscle fatigue and unopposed sympathetic vasoconstriction during exercise, thereby increasing contraction-induced damage in dystrophin-deficient muscles. The loss of normal nNOS signaling during exercise is central to the vascular dysfunction proposed to be an important pathogenic mechanism in DMD. Eventual loss of cardiac function often leasds to hear failure in DMD patients.

Currently, there is a largely unmet need for an effective way of treating cardiovascular disease and disorders (e.g. congestive heart disease), and diseases and disorders which may result in cardiac dysfunction or cardiomyopathy (e.g., Duchenne Muscular Dystrophy). Improved therapeutic compounds, compositions and methods for the treatment of cardiac conditions and dysfunction are urgently required.

Eleven families of phosphodiesterases (PDEs) have been identified but only PDEs in Family I, the $Ca^{2+}$-calmodulin-dependent phosphodiesterases (CaM-PDEs), which are activated by the $Ca^{2+}$-calmodulin and have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it is also detected in the heart, is present in neutrophils and has been shown to be involved in inflammatory responses of this cell. PDE1C is expressed in olfactory epithelium, cerebellar granule cells, striatum, heart, and vascular smooth muscle. PDE1C is a major phosphodiesterase in the human cardiac myocyte.

Of all of the PDE families, the major PDE activity in the human cardiac ventricle is PDE1. Generally, there is a high abundance of PDE1 isoforms in: cardiac myocytes, vascular endothelial cells, smooth muscle cells, fibroblasts and motor neurons. Up-regulation of phosphodiesterase 1A expression is associated with the development of nitrate tolerance. Kim et al., *Circulation* 104(19:2338-2343 (2001). Cyclic nucleotide phosphodiesterase 1C promotes human arterial smooth muscle cell proliferation. Rybalkin et al., *Circ. Res.* 90(2): 151-157 (2002). The cardiac ischemia-reperfusion rat model also shows an increase in PDE1 activity. Kakkar et al., can. *J. Physiol. Pharmacol.* 80(1):59-66 (2002). $Ca^{2+}$/CaM-stimulated PDE1, particularly PDE1A has been shown to be involved in regulating pathological cardiomyocyte hypertrophy. Millet et al., *Circ. Res.* 105(10):956-964 (2009). Early cardiac hypertrophy induced by angiotensin II is accompanied by 140% increases in PDE1A in a rat model of heart failure. Mokni et al., *Plos. One.* 5(12):e14227 (2010). Inhibition of phosphodiesterase 1 augments the pulmonary vasodilator response to inhaled nitric oxide in awake lambs with acute pulmonary hypertension. Evgenov et al., *Am. J. Physiol. Lung Cell. Mol. Physiol.* 290(4):L723-L729 (2006). Strong upregulation of the PDE1 family in pulmonary artery smooth muscle cells is also noted in human idiopathic PAH lungs and lungs from animal models of PAH. Schermuly et al., *Circulation* 115(17)2331-2339 (2007). PDE1A and 1C, found in fibroblasts, are known to be up-regulated in the transition to the "synthetic phenotype", which is connected to the invasion of diseased heart tissue by pro-inflammatory cells that will deposit extracellular matrix. PDE1B2, which is present in neutrophils, is up-regulated during the process of differentiation of macrophages. Bender et al., *PNAS* 102(2):497-502 (2005). The differentiation of monocytes to macrophage, in turn, is involved in the inflammatory component of heart disease, particularly atherothrombosis, the underlying cause of approximately 80% of all sudden cardiac death. Willerson et al., *Circulation* 109:II-2-1140 (2004).

Cyclic nucleotide phosphodiesterases downregulate intracellular cAMP and cGMP signaling by hydrolyzing these cyclic nucleotides to their respective 5'-monophosphates (5'AMP and 5'GMP). cGMP is a central intracellular second-messenger regulating numerous cellular functions. In the cardiac myocyte, cGMP mediates the effects of nitric oxide and atrial natriuretic peptide, whereas its counterpart, cAMP, mediates catecholamine signaling. Each cyclic nucleotide has a corresponding primary targeted protein kinase, PKA for cAMP, and PKG for cGMP. PKA stimulation is associated with enhanced contractility and can stimulate growth, whereas PKG acts as a brake in the heart, capable of countering cAMP-PKA-contractile stimulation and inhibiting hypertrophy. Importantly, the duration and magnitude of these signaling cascades are determined not only by generation of cyclic nucleotides, but also by their hydrolysis catalyzed by phosphodiesterases (PDEs). PDE regulation is quite potent—often suppressing an acute rise in a given cyclic nucleotide back to baseline within seconds. It is also compartmentalized within the cell, so that specific targeted proteins can be regulated by the same "generic" cyclic nucleotide. By virtue of its modulation of cGMP in the myocyte, PDE1 participates in hypertrophy regulation. (Circ Res. 2009, Nov. 6; 105(10):931).

One of the challenges currently faced in the field is the lack of PDE1 specific inhibitors. The current invention seeks to overcome this as well as other challenges in the art by providing PDE1 specific inhibitors. Although WO 2006/133261 and WO 2009/075784 provide PDE1 specific inhibitors, these do not disclose the compounds of the current invention.

SUMMARY OF THE INVENTION

PDE1 is up-regulated in chronic disease conditions such as atherosclerosis, cardiac pressure-load stress and heart failure, as well as in response to long-term exposure to nitrates. PDE1 inhibitors have relatively little impact on resting function, but rather maintain the ability to potently modulate acute contractile tone in cells stimulated by vaso-active agonists. Such up-regulation contributes to vascular and cardiac pathophysiology and to drug tolerance to nitrate therapies. Therefore, without being bound by theory, it is believed that compounds that modulate cGMP/PKG mediated pathways, such as PDE1 inhibitors, are particularly useful for reversing cardiac hypertrophy. The PDE1 inhibitors disclosed herein are selective PDE1 inhibitors having a limited ability to penetrate the blood brain barrier and therefore, are believed to have significant modulatory activity (e.g., enhancement of cGMP) in those areas of the body outside of the central nervous system where PDE1 isoforms are predominately located: e.g., cardiac, vascular, and lung tissue.

Therefore, in the first aspect, the invention provides a compound of Formula I:

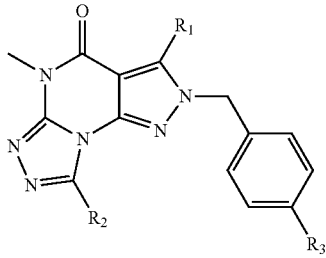

Formula I in free or salt form, wherein
(i) $R_1$ is —NH($R_4$), wherein $R_4$ is phenyl optionally substituted with halo (e.g., fluoro), for example, 4-fluorophenyl;
(ii) $R_2$ is H or $C_{1-6}$alkyl (e.g., methyl or ethyl);
(iii) $R_3$ is H, halogen (e.g., bromo), $C_{1-6}$alkyl (e.g., methyl), aryl optionally substituted with halogen (e.g., 4-fluorophenyl), heteroaryl optionally substituted with halogen (e.g., 6-fluoropyrid-2-yl or pyrid-2-yl), or acyl (e.g., acetyl),
in free or salt form.

In a particular embodiment, the invention provides a compound of Formula I as follows:
1.1 the compound of Formula I, wherein $R_1$ is —NH($R_4$) wherein $R_4$ is phenyl optionally substituted with halo (e.g., fluoro), for example, 4-fluorophenyl;
1.2 the compound of Formula I or 1.1, wherein $R_4$ is phenyl;
1.3 the compound of Formula I or 1.1, wherein $R_4$ is 4-fluorophenyl;
1.4 the compound of Formula I or any of Formulas 1.1-1.3, wherein $R_2$ is $C_{1-6}$alkyl (e.g., methyl or ethyl);
1.5 the compound of Formula I or any of Formulas 1.1-1.4, wherein $R_2$ is methyl;
1.6 the compound of Formula I or any of Formulas 1.1-1.4, wherein $R_2$ is ethyl;
1.7 the compound of Formula I or any of Formulas 1.1-1.3, wherein $R_2$ is H;
1.8 the compound of Formula I or any of Formulas 1.1-1.7, wherein $R_3$ is $C_{1-6}$alkyl (e.g., methyl);
1.9 the compound of Formula I or any of Formulas 1.1-1.7, wherein $R_3$ is halogen (e.g., bromo);
1.10 the compound of Formula I or any of Formulas 1.1-1.7, wherein $R_3$ is heteroaryl optionally substituted with halogen;
1.11 the compound of Formula I or any of Formulas 1.1-1.7, wherein $R_3$ is pyrid-2-yl;
1.12 the compound of Formula I or any of Formulas 1.1-1.7, wherein $R_3$ is 6-fluoro-pyrid-2-yl;
1.13 the compound of Formula I or any of Formulas 1.1-1.7, wherein $R_3$ is acyl (e.g., acetyl);
1.14 the compound of Formula I or any of Formulas 1.1-1.13, wherein the compound is:

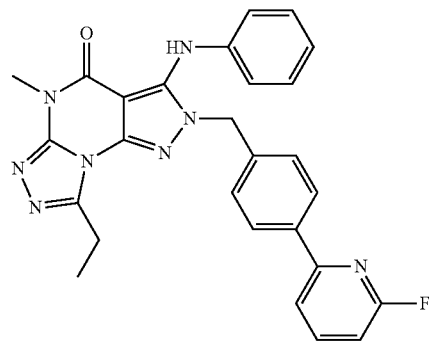 [SMILES: CCc1nnc2n(C)c(=O)c3c(Nc4ccccc4)n(Cc4ccc(-c5cccc(F)n5)cc4)nc3n12]

1.15 the compound of Formula I or any of Formulas 1.1-1.13, wherein the compound is:

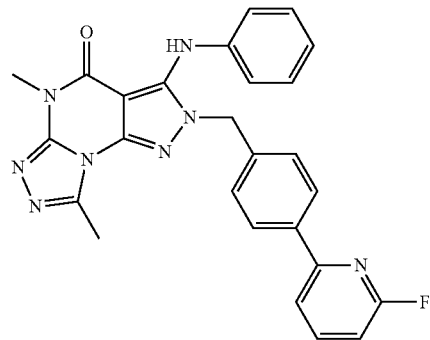 [SMILES: Cc1nnc2n(C)c(=O)c3c(Nc4ccccc4)n(Cc4ccc(-c5cccc(F)n5)cc4)nc3n12]

1.16 the compound of Formula I or any of Formulas 1.1-1.3, wherein the compound is:

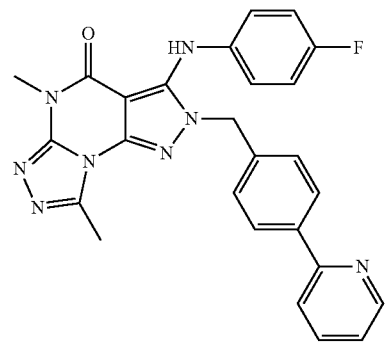 [SMILES: Cc1nnc2n(C)c(=O)c3c(Nc4ccc(F)cc4)n(Cc4ccc(-c5ccccn5)cc4)nc3n12]

1.17 the compound of Formula I or any of Formulas 1.1-1.13, wherein the compound is:

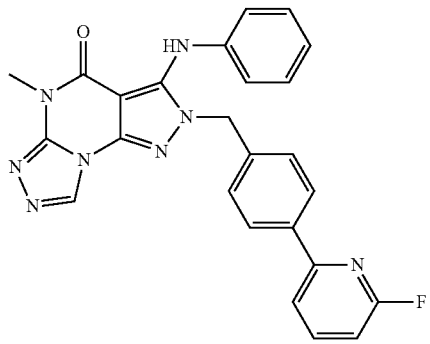 [SMILES: Cn1c(=O)c2c(Nc3ccccc3)n(Cc3ccc(-c4cccc(F)n4)cc3)nc2n2cnnc12]

in free or salt form.

In the second aspect, the invention provides a pharmaceutical composition comprising the compound of Formula I or any of 1.1-1.17 as described herein, in free or pharmaceutically acceptable salt form, in admixture with a pharmaceutically acceptable diluents or carrier.

The compound of Formula I or any of 1.1-1.17 as described herein are selective PDE1 inhibitors and therefore are useful for regulating cGMP/PKG in cardiac hypertrophy. Previous studies have demonstrated that increases in intracellular $Ca^{2+}$/CaM-dependent signaling promote maladaptive hypertrophic gene expression in cardiomyocytes through various effectors such as the protein phosphatase calcineurin, $Ca^{2+}$/CaM-dependent kinase II (CaMKII). Without being bound by any theory, increases in endogenous cGMP/PKG-dependent signaling may be able to decrease cardiac hypertrophy, by suppressing Gq/11 activation and normalizing $Ca^{2+}$ signaling. By activating PDE1, $Ca^{2+}$/CaM may decrease cGMP levels and PKG activity. In turn, this process may drive cardiac hypertrophy. Additionally, up-regulation of PDE1 expression upon neurohumoral or biomechanical stress during cardiac hypertrophy may further enhance PDE1 activity and attenuate cGMP/PKG signaling. Accordingly, without being bound by any theory, it is believed that inhibition of PDE1A could, for example, reverse or prevent the attenuation of cGMP/PKG signaling. As discussed previously, PDE1B is also implicated in the inflammatory component of heart disease (e.g., PDE1B2 is up-regulated during the process of differentiation of macrophages, as occurs during heart disease progression). Similarly, PDE1C is induced in human arterial smooth muscle cells of the synthetic, proliferative phenotype. Therefore, administration of a PDE1 inhibitor as described herein could provide a potential means to regulate cardiac hypertrophy, and by extension provide a treatment for various cardiovascular diseases and disorders.

Therefore, in the third aspect, the invention provides a method for the treatment or prophylaxis of a disease or disorder which may be ameliorated by modulating (e.g., enhancing) cGMP/PKG-dependent signaling pathways (e.g., in cardiac tissue), e.g. a cardiovascular disease or disorder, comprising administering to a patient in need thereof an effective amount of the compound of Formula I or any of formulae 1.1-1.17 as described herein, in free or pharmaceutically acceptable salt form.

The cardiovascular disease or disorder may be selected from a group consisting of: hypertrophy (e.g., cardiac hypertrophy), atherosclerosis, myocardial infarction, congestive heart failure, angina, stroke, hypertension, essential hypertension, pulmonary hypertension, pulmonary arterial hypertension, secondary pulmonary hypertension, isolated systolic hypertension, hypertension associated with diabetes, hypertension associated with atherosclerosis, renovascular hypertension. In certain embodiments, the cardiovascular disease or disorder to be treated may also relate to impaired cGMP/PKG-dependent signaling. In a particular embodiment, the invention provides a method for the treatment or prevention of stroke, wherein the PDE1 inhibitor, through its effect on the endothelial cells of cerebral capillaries, is able to promote increased cerebral blood flow.

In a further embodiment of the third aspect, the invention also provides a method for the treatment or prophylaxis of cardiovascular disease or disorder that is associated with a muscular dystrophy (e.g, Duchenne, Becker, limb-girdle, myotonic, and Emery-Dreifuss Muscular Dystrophy) comprising administering to a patient in need thereof an effective amount of the compound of Formula I or any of 1.1-1.17 as described herein, in free or pharmaceutically acceptable salt form. As noted above, DMD is caused by the absence of a functional dystrophin protein, which in turn leads to reduced expression and mis-localization of dystrophin-associated proteins, such as neuronal nitric oxide (NO) synthase. Disruption of nNOS signaling may result in muscle fatigue and unopposed sympathetic vasoconstriction during exercise, thereby increasing contraction-induced damage in dystrophin-deficient muscles. Without being bound by theory, the loss of normal nNOS signaling during exercise may be central to the vascular dysfunction proposed to be an important pathogenic mechanism in DMD. It is contemplated that by inhibiting phosphodiesterases (e.g. PDE1), the compounds described herein may circumvent defective nNOS signaling in dystrophic skeletal and/or cardiac muscle; thereby potentially improving cardiac outcomes in DMD patients.

In still another embodiment, the invention provides for the treatment of renal failure, fibrosis, inflammatory disease or disorders, vascular remodeling and connective tissue diseases or disorders (e.g., Marfan Syndrome), comprising administering to a patient in need thereof an effective amount of the compound of Formula I or any of formulae 1.1-1.17 as described herein, in free or pharmaceutically acceptable salt form.

The PDE1 compounds of the invention useful for the treatment or prophylaxis of disease according to the foregoing methods may be used as a sole therapeutic agent or may be used in combination with one or more other therapeutic agents useful for the treatment of cardiovascular disorders. Such other agents include angiotensin II receptor antagonists, angiotensin-converting-enzyme (ACE) inhibitors, neutral endopeptidase (NEP or Neprilysin) inhibitors and/or phosphodiesterase 5 (PDE5) inhibitors.

Therefore, in a particular embodiment, the PDE1 inhibitor of the invention may be administered in combination with an angiotensin II receptor antagonist selected from azilsartan, candesartan, eprosartan, irbesartan, losartan, olmesartan, olmesartan medoxomil, saralasin, telmisartan and valsartan, in free or pharmaceutically acceptable salt form.

In yet another embodiment, the PDE1 inhibitor of the invention may be administered in combination with an angiotensin-converting-enzyme (ACE) inhibitor selected from the group consisting of: captopril, enalapril, lisinopril, benazepril, ramipril, quinapril, peridopril, imidapril, trandolapril and cilazapril, in free or pharmaceutically acceptable salt form.

In still another particular embodiment, the PDE1 inhibitor of the invention may be administered in combination with a PDE5 inhibitor selected from avanafil, lodenafil, mirodenafil, tadalafil, vardenafil, udenafil and zaprinast, in free or pharmaceutically acceptable salt form.

In still another particular embodiment, the PDE1 inhibitor of the invention may be administered in combination with a neutral endopeptidase (NEP or Neprilysin) inhibitor. Neutral endopeptidase, also known as Neprilysin or NEP (EC 3.4.24.11), is a type II integral membrane zinc-dependent metalloendoprotease that cleaves a variety of short peptide substrates. Among its natural targets are cardiac atrial natriuretic peptide (ANP), B-type natriuretic peptide (BNP), C-type natriuretic peptide (CNP), angiotensin I (Ang-I), angiotensin II (Ang-II), bradykinin (BK), and endothelin (ET). Cleavage of these peptides by NEP results in their inactivation, attenuating the peptides' natural biological effects.

ANP, BNP and CNP are all part of the natriuretic peptide (NP) system, which, along with the renin-angiotensin system, is a major component of mammalian blood pressure homeostasis. While the renin-angiotensin system is primarily responsible for increasing blood pressure (e.g., by promoting vasoconstriction and water retention), the natriuretic peptide system is primarily responsible for decreasing blood pressure (e.g., by promoting vasodilation and natriuresis). ANP and BNP are both powerful vasodilators and strong promoters of decreased renal reabsorption of sodium and water in a potassium-sparing manner. These dual effects exert a powerful blood pressure lowering effect. BNP and CNP also exert an anti-fibrotic effect and an anti-hypertrophic effect in the heart. CNP shares the vasodilatory effects of ANP/BNP but without the renal effects.

In addition, both hypertension and obesity have been shown to be associated with reduced ANP and BNP levels, and a specific genetic variant of ANP (rs5068), which increases ANP levels, has been shown to protect against hypertension and metabolic syndrome. Thus, ANP, BNP and CNP play an important role in blood pressure homeostasis and cardiovascular health.

Inhibition of NEP results in an increase in the half-lives of circulating ANP, BNP and CNP. This is expected to prolong their blood-pressure lowering and cardiac health improving effects. Urine cAMP levels ae significantly elevated after systemic administration of NEP inhibitors.

Inhibition of NEP also results in higher levels of bradykinin, angiotensin I, angiotensin II and endothelin. Importantly, endothelin and angiotensin II are strongly pro-hypertensive peptides. Thus, NEP inhibition alone results in both vasodilatory effects (from the NPs) and vasoconstrictive effects (from increased Ang-II and ET). These pro-hypertensive peptides all operate via binding to G-protein coupled receptors (GPCRs). The major contributor to this vasoconstrictive effect is Angiotensin-II, which operates via binding to the G-protein coupled receptors $AT_1$ and $AT_2$. These receptors exert their physiological effects through activation of phospholipase C (PLC) and protein kinase C (PKC) signaling cascades. Bradykinin is inactivated to a large extent by ACE, and ACE inhibitors cause congestion as a major side effect, which is not seen with NEP inhibitors.

ANP, BNP and CNP all function via the second messenger cGMP. ANP and BNP bind to membrane-bound guanylyl cyclase-A, while CNP binds to guanylyl cyclase B. Both of these enzymes increase intracellular cGMP in response to receptor binding. The increased cGMP concentration activates protein kinase G (PKG) which is responsible for exerting the downstream biological effects of the natriuretic peptides.

Several NEP inhibitors are known, including candoxatril, candoxatrilat, omepatrilat, gempatrilat, and sampatrilat. Candoxtrail had been shown to produce a dose-dependent increase in both plasma ANP and cGMP levels, and although it is safe, it does not produce a stable blood-pressure lowering effect. This is thought to be due to the effects of NEP inhibition on BK, ET and Ang-II breakdown. Candoxatril treatment in patients with heart failure has been shown to increase levels of endothelin significantly, thus cancelling out the blood pressure effects caused by increased ANP.

In contrast to candoxatril and candoxatrilat, omapatrilat is considered a vasopeptidase inhibitor (VPI), because it functions to an equal extent as both an NEP inhibitor and an ACE (angiotensin converting enzyme) inhibitor. ACE is the enzyme that is responsible for converting Ang-I to Ang-II, which is the major pro-hypertensive hormone of the renin-angiotensin system. By both inhibiting NEP and ACE, it was thought that the increase in Ang-II caused by NEP inhibition would be negated, resulting in a highly effective antihypertensive treatment. Clinical studies, however, showed that omapatrilat was associated with a severe incidence of angioedema (a known side effect of ACE inhibitors). Later research has indicated that this may be due to concomitant inhibition of aminopeptidase P (APP). ACE, APP and NEP all contribute to the breakdown of bradykinin, which is another anti-hypertensive peptide, and the over-accumulation of bradykinin resulting from simultaneous inhibition of three of its degradation pathways may be a strong factor leading to angioedema.

Without intending to be bound by any particular theory, the combination of a PDE1 inhibitor with a selective NEP inhibitor (not a VPI) should realize the full positive effects of NEP inhibition (increased ANP, BNP and CNP half-life), further enhanced by the potentiation of the NP signaling cascades (mediated by cGMP) caused by PDE1 inhibition, without the negative effects of NEP inhibition that can lead to decreased efficacy.

Therefore, in a particular embodiment, the neutral endopeptidase (NEP or Neprilysin) inhibitor useful for the invention is a selective NEP inhibitor, e.g., with at least 300-fold selectivity for NEP inhibition over ACE inhibition. In a further embodiment, the NEP inhibitors for use in the current invention are inhibitors with at least 100-fold selectivity for NEP inhibition over ECE (Endothelin Converting Enzyme) inhibition. In yet another embodiment, the NEP inhibitors for use in the current invention are inhibitors with at least 300-fold selectivity for NEP inhibition over ACE inhibition and 100-fold selectivity for NEP inhibition over ECE inhibition.

In another embodiment, the NEP inhibitors for use in the current invention are the NEP inhibitors disclosed in the following publications: EP-1097719 B1, EP-509442A, U.S. Pat. No. 4,929,641, EP-599444B, US-798684, J. Med. Chem. (1993) 3821, EP-136883, U.S. Pat. No. 4,722,810, Curr. Pharm. Design (1996) 443, J. Med. Chem. (1993) 87, EP-830863, EP-733642, WO 9614293, WO 9415908, WO 9309101, WO 9109840, EP-519738, EP-690070, Bioorg. Med. Chem. Lett. (1996) 65, EP-A-0274234, Biochem. Biophys. Res. Comm. (1989) 58, Perspect. Med. Chem. (1993) 45, or EP-358398-B. The contents of these patents and publications are hereby incorporated by reference in their entirety herein.

In still another embodiment, the NEP inhibitors useful in the current invention are the NEP inhibitors Phosphoramidon, Thiorphan, Candoxatrilat, Candoxatril, or the compound of the Chemical Abstract Service (CAS) Number 115406-23-0.

In yet another embodiment, the NEP inhibitors useful in the current invention are the NEP inhibitors disclosed in US 2006/0041014 A1, the contents of which are hereby incorporated by reference in their entirety herein.

In another embodiment, the NEP inhibitors useful in the current invention are the NEP inhibitors disclosed in U.S. Pat. No. 5,217,996, the contents of which are hereby incorporated by reference in their entirety herein.

In another embodiment, the NEP inhibitors useful in the current invention are the NEP inhibitors disclosed in U.S. Pat. No. 8,513,244, the contents of which are hereby incorporated by reference in their entirety herein.

In another embodiment, the NEP inhibitors useful in the current invention are the NEP inhibitors disclosed in U.S. Pat. No. 5,217,996, the contents of which are hereby incorporated by reference in their entirety herein.

In another embodiment, the NEP inhibitors useful in the current invention are the NEP inhibitors disclosed in US patent application publication 2013/0330365, the contents of which are hereby incorporated by reference in their entirety herein.

In another embodiment, the NEP inhibitor useful in the current invention is 3-[{1S,5R}-1-biphenyl-4ylmethyl-3-ethoxycarbonyl-1-butylcarbamoyl]propionic acid,

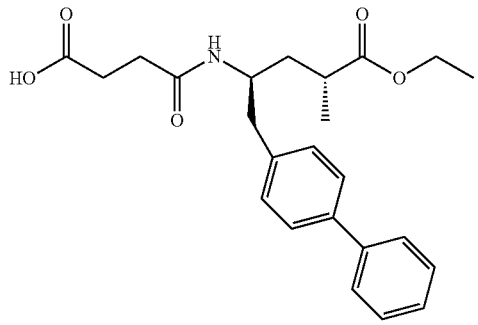 [SMILES: CCOC(=O)[C@H](C)C[C@@H](Cc1ccc(-c2ccccc2)cc1)NC(=O)CCC(=O)O]

also known as AHU-377, in free or a pharmaceutically acceptable salt or prodrug, thereof, and in a preferred embodiment thereof, in sodium salt form.

In another embodiment, the NEP inhibitor useful in the current invention is [2R, 4R}-1-biphenyl-4ylmethyl-3-carboxy-1-butylcarbamoyl]propionic acid,

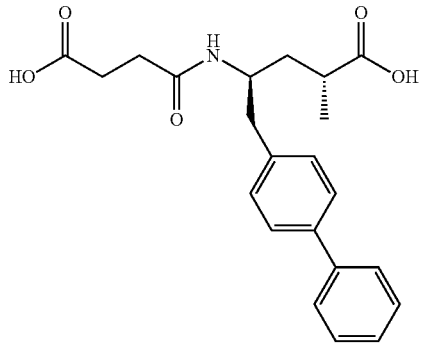 [SMILES: C[C@H](C[C@@H](Cc1ccc(-c2ccccc2)cc1)NC(=O)CCC(=O)O)C(=O)O]

also known as LBQ-657, in free or pharmaceutically acceptable ester, salt or prodrug form.

In another embodiment, the NEP inhibitor useful in the current invention is selected from among the following: sampatrilat, fasidotril, Z13752A, MDL 100240, BMS 189921, LBQ657, AHU-377, or mixanpril, in free or pharmaceutically acceptable salt form or in prodrug form thereof.

In another embodiment, the NEP inhibitor for use in the current invention is selected from the following:

SQ 28,603;
N—[N-[1(S)-carboxyl-3-phenylpropyl]-(S)-phenylalanyl]-(S)-isoserine;
N—[N-[((1S)-carboxy-2-phenyl)ethyl]-(S)-phenylalanyl]-beta-alanine;
N-[2(S)-mercaptomethyl-3-(2-methylphenyl)-propionyl] methionine;
(cis-4-[[[1-[2-carboxy-3-(2-methoxy-ethoxy)propyl]-cyclopentyl]carbonyl]amino]-cyclohexanecarboxylic acid);
thiorphan; retro-thiorphan; phosphoramidon; SQ 29072;
N-(3-carboxy-1-oxopropyl)-(4S)-p-phenylphenylmethyl)-4-amino-2R-methylbutanoic acid ethyl ester;
(S)-cis-4-[1-[2-(5-indanyloxycarbonyl)-3-(2-methoxyethoxy)propyl]-1-cyclopentanecarboxamido]-1-cyclohexanecarboxylic acid;
3-(1-[6-endo-hydroxymethyl-bicyclo[2,2,1]heptane-2-exo-carbamoyl]cyclopentyl)-2-(2-methoxyethyl)propanoic acid;
N-(1-(3-(N-t-butoxycarbonyl-(S)-prolylamino)-2(S)-t-butoxy-carbonylpropyl)cyclopentanecarbonyl)-O-benzyl-(S)-serine methyl ester;
4-[[2-(mercaptomethyl)-1-oxo-3-phenylpropyl]amino] benzoic acid;
3-[1-(cis-4-carboxycarbonyl-cis-3-butylcyclohexyl-r-1-carbamoyl)cyclopentyl]-2S-(2-methoxyethoxymethyl) propanoic acid;
N-((2S)-2-(4-biphenylmethyl)-4-carboxy-5-phenoxyvaleryl)glycine;
N-(1-(N-hydroxycarbamoylmethyl)-1-cyclopentanecarbonyl)-L-phenylalanine;
(S)-(2-biphenyl-4-yl)-1-(1H-tetrazol-5-yl)ethylamino) methylphosphonic acid;
(S)-5-(N-(2-(phosphonomethylamino)-3-(4-biphenyl) propionyl)-2-aminoethyl)tetrazole;
beta-alanine;
3-[1,1'-biphenyl]-4-yl-N-[(diphenoxyphosphinyl)methyl]-L-alanyl;
N-(2-carboxy-4-thienyl)-3-mercapto-2-benzylpropanamide;
2-(2-mercaptomethyl-3-phenylpropionamido)thiazol-4-ylcarboxylic acid;
(L)-(1-((2,2-dimethyl-1,3-dioxolan-4-yl)-methoxy)carbonyl)-2-phenylethyl)-L-phenylalanyl)-beta-alanine;
N—[N—[(L)-[1-[(2,2-dimethyl-1,3-dioxolan-4-yl)-methoxy]carbonyl]-2-phenylethyl]-L-phenylalanyl]-(R)-alanine;
N—[N—[(L)-1-carboxy-2-phenylethyl]-L-phenylalanyl]-(R)-alanine;
N-[2-acetylthiomethyl-3-(2-methyl-phenyl)propionyl]-methionine ethyl ester;
N-[2-mercaptomethyl-3-(2-methylphenyl)propionyl]-methionine;
N-[2(S)-mercaptomethyl-3-(2-methylphenyl)propanoyl]-(S)-isoserine;
N—(S)-[3-mercapto-2-(2-methylphenyl)propionyl]-(S)-2-methoxy-(R)-alanine;
N-[1-[[1(S)-benzyloxy-carbonyl-3-phenylpropyl]amino] cyclopentylcarbony1]—(S)-isoserine;

N-[1-[[1(S)-carbonyl-3-phenylpropyl]amino]-cyclopentylcarbonyl]-(S)-isoserine;
1,1'-[dithiobis-[2(S)-(2-methylbenzyl)-1-oxo-3,1-propanediyl]]-bis-(S)-isoserine;
1,1'-[dithiobis-[2(S)-(2-methylbenzyl)-1-oxo-3, 1-propanediyl]]-bis-(S)-methionine;
N-(3-phenyl-2-(mercaptomethyl)-propionyl)-(S)-4-(methylmercapto)methionine;
N-[2-acetylthiomethyl-3-phenyl-propionyl]-3-aminobenzoic acid;
N-[2-mercaptomethyl-3-phenyl-propionyl]-3-aminobenzoic acid;
N-[1-(2-carboxy-4-phenylbutyl)-cyclopentane-carbonyl]-(S)-isoserine;
N-[1-(acetylthiomethyl)cyclopentane-carbonyl]-(S)-methionine ethyl ester;
3(S)-[2-(acetylthiomethyl)-3-phenyl-propionyl]amino-epsilon-caprolactam;
N-(2-acetylthiomethy 1-3-(2-methylphenyl)propionyl)-methionine ethyl ester; in free or pharmaceutically acceptable salt form.

In another aspect, the invention provides the following:
(i) the compound of Formula I or any of 1.1-1.17 as described herein, in free or pharmaceutically acceptable salt form, for use in any of the methods or in the treatment or prophylaxis of any disease or disorder as set forth herein,
(ii) a combination as described hereinbefore, comprising a PDE1 inhibitor of the invention, e.g., the compound of Formula I or any of 1.1-1.17 as described herein, in free or pharmaceutically acceptable salt form and a second therapeutic agent useful for the treatment of cardiovascular disorders, e.g., selected from angiotensin II receptor antagonist, angiotensin-converting-enzyme (ACE) inhibitor, neutral endopeptidase (NEP or Neprilysin) inhibitor and/or phosphodiesterase 5 (PDE5) inhibitor, in free or pharmaceutically acceptable salt form;
(iii) use of the compound of Formula I or any of 1.1-1.17, in free or pharmaceutically acceptable salt form, or the combination described herein, (in the manufacture of a medicament) for the treatment or prophylaxis of any disease or condition as set forth herein,
(iv) the compound of Formula I or any of 1.1-1.17, in free or pharmaceutically acceptable salt form, the combination described herein or the pharmaceutical composition of the invention as hereinbefore described for use in the treatment or prophylaxis of any disease or condition as set forth herein.

DETAILED DESCRIPTION OF THE INVENTION

If not otherwise specified or clear from context, the following terms herein have the following meanings:
(a) "Alkyl" as used herein is a saturated or unsaturated hydrocarbon moiety, preferably saturated, preferably having one to six carbon atoms, in some embodiment, one to four carbon atoms, which may be linear or branched, and may be optionally mono-, di- or tri-substituted, e.g., with halogen (e.g., chloro or fluoro) or hydroxy.

Compounds of the Invention, e.g., the compound of Formula I or any of formulae 1.1-1.17 as described herein, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$ alkyl can hydrolyze to form Compound-C(O)OH and HO—$C_{1-4}$alkyl. As will be appreciated the term thus embraces conventional pharmaceutical prodrug forms.

The Compounds of the Invention include their enantiomers, diastereomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$ $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Melting points are uncorrected and (dec) indicates decomposition. Temperature are given in degrees Celsius (° C.);

unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Methods of Using Compounds of the Invention

The Compounds of the Invention are useful in the treatment of diseases characterized by disruption of or damage to cGMP/PKG mediated pathways, e.g., as a result of increased expression of PDE1 or decreased expression of cGMP/PKG activity due to inhibition or reduced levels of inducers of cyclic nucleotide synthesis, such as dopamine and nitric oxide (NO). It is believed that by inhibiting PDE1A or PDE1C, for example, that this action could reverse or prevent the attenuation of cGMP/PKG signaling (e.g., enhance cGMP) and that this action could modulate cardiac hypertrophy. Therefore, administration or use of the PDE1 inhibitor as described herein, e.g., a Compound of Formula 1.1-1.17 as described herein, in free or pharmaceutically acceptable salt form, could provide a potential means to regulate cardiac hypertrophy (e.g., prevent and/or reverse cardiac hypertrophy), and in certain embodiments provide a treatment for various cardiovascular diseases and disorders.

The PDE1 inhibitors of the present invention generally are selective for PDE1 (generally off-target interactions >10×, more preferably >25×, still more preferably >100× affinity for PDE1), exhibit good oral availability in plasma with very minimal brain penetration in mice. The blood/plasma ratio in mice administered the PDE1 inhibitors of the present invention is preferably less than 0.4, more preferably less than 0.2, more preferably less than or equal to 0.1.

The PDE1 inhibitor of the invention (i.e., Formula I as hereinbefore described) may be used in a combination therapy wherein the PDE1 inhibitor may be administered simultaneously, separately or sequentially with another active agent. Therefore, the combination can be a free combination or a fixed combination.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

The dosages of a compound of the invention in combination with another active agent can be the same as or lower than the approved dosage for the drug, the clinical or literature test dosage or the dosage used for the drug as a monotherapy. The dosage amount will be apparent to one skilled in the art.

Diseases and disorders that may be prevented or ameliorated by the enhancement of cGMP/PKG signaling (e.g., cardiovascular disease), e.g., using the Compound of the Invention as described herein, include, but are not limited to: hypertrophy (e.g., cardiac hypertrophy), atherosclerosis, myocardial infarction, congestive heart failure, angina, stroke, hypertension, essential hypertension, pulmonary hypertension, pulmonary arterial hypertension, secondary pulmonary hypertension, isolated systolic hypertension, hypertension associated with diabetes, hypertension associated with atherosclerosis, renovascular hypertension, renal failure, fibrosis, an inflammatory disease or disorder, vascular remodeling, and an connective tissue disease or disorder (e.g., Marfan Syndrome).

In one embodiment, the Compounds of the Invention as described herein are useful in the treatment or prevention of stroke by treating or preventing transient ischemic attacks (TIA). Without being bound by any theory, it is believed that the Compounds of the Invention may prevent or treat the risk of transient ischemic attacks by actually increasing the amount and/or concentration of blood flow to the brain. It is contemplated that the compounds as described herein could increase the blood flow to the brain without significant passage across the blood brain barrier.

In another embodiment, the invention further provides using the Compounds of the Invention for the treatment or prevention of disease or disorder as follows: Duchenne muscular dystrophy, Becker muscular dystrophy, limb-girdle muscular dystrophy, myotonic dystrophy, and Emery-Dreifuss muscular dystrophy. In one embodiment, the Compounds of the Invention are useful in treating cardiac dysfunction associated with aforementioned types of muscular dystrophy. In another embodiment, the Compounds of the Invention may potentially reduce or reverse the cardiac hypertrophy that may be associated with these aforementioned types of muscular dystrophy.

"PDE1 inhibitor" as used herein describes a compound of Formula I or any of formulae 1.1-1.17. which selectively inhibit phosphodiesterase-mediated (e.g., PDE1-mediated, especially PDE1B-mediated) hydrolysis of cGMP, e.g., with an $IC_{50}$ of less than 1 μM, preferably less than 75 nM, preferably less than 1 nM, in an immobilized -metal affinity particle reagent PDE assay as described or similarly described in Example 1.

The phrase "Compounds of the Invention" or "PDE 1 inhibitors of the Invention", or like terms, encompasses any and all of the compounds disclosed herewith, e.g., a Compound of Formula I or any of formulae 1.1-1.17, in free or salt form.

The words "treatment" and "treating" are to be understood accordingly as embracing treatment or amelioration of symptoms of disease as well as treatment of the cause of the disease.

For methods of treatment, the word "effective amount" is intended to encompass a therapeutically effective amount to treat a specific disease or disorder.

The term "patient" include human or non-human (i.e., animal) patient. In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

Compounds of the Invention, e.g., compounds of Formula I or any of formulas 1.1-1.17 as hereinbefore described, in free or pharmaceutically acceptable salt form, may be used

17 as a sole therapeutic agent, but may also be used in combination or for co-administration with other active agents.

Dosages employed in practicing the present invention will of course vary depending, e.g. on the particular disease or condition to be treated, the particular compound used, the mode of administration, and the therapy desired. The compound may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 300 mg, conveniently administered once, or in divided doses 2 to 4 times, daily or in sustained release form. Unit dosage forms for oral administration thus for example may comprise from about 0.2 to 75 or 150 mg or 300 mg, e.g. from about 0.2 or 2.0 to 10, 25, 50, 75, 100, 150, 200 or 300 mg of the compound disclosed herein, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

Methods of Making Compounds of the Invention

The compounds of the Invention and their pharmaceutically acceptable salts may be made using the methods as described and exemplified herein and/or by methods similar thereto and/or by methods known in the chemical art. Such methods include, but not limited to, those described below. If not commercially available, starting materials for these processes may be made by procedures, which are selected from the chemical art using techniques which are similar or analogous to the synthesis of known compounds.

Various NEP inhibitors and starting materials therefor may be prepared using methods described in US 2006-0041014 A1, EP 1097719 A1, U.S. Pat. No. 8,513,244, and US 2013-0330365 A1. All references cited herein are hereby incorporated by reference in their entirety.

Various starting materials and/or Compounds of the Invention may be prepared using methods described in WO 2006/133261 and WO 2009/075784. All references cited herein are hereby incorporated by reference in their entirety.

Terms and Abbreviations

DMF=N,N-dimethylforamide,
MeOH=methanol,
THF=tetrahydrofuran,
equiv.=equivalent(s),
h=hour(s),
HPLC=high performance liquid chromatography,
LiHMDS=lithium bis(trimethylsilyl)amide,
NMP=1-methyl-2-pyrrolidinone,
Pd$_2$(dba)$_3$=tris[dibenzylideneacetone]dipalladium(0)
TFA=trifluoroacetic acid,
TFMSA=trifluoromethanesulfonic acid

18

EXAMPLES

Example 1

8-Ethyl-2-(4-(6-fluoro-pyridin-2-yl)-benzyl)-5-methyl-3-phenylamino-2H,5H-pyrazolo[4,3-e][1,2,4]triazolo[4,3-a]pyrimidin-4-one

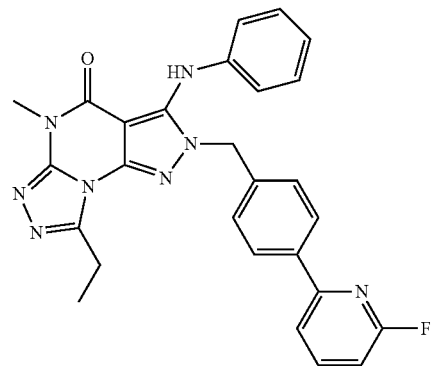 [SMILES: CCc1nnc2n(C)c(=O)c3c(Nc4ccccc4)n(Cc4ccc(-c5cccc(F)n5)cc4)nc3n12]

(a) 6-Chloro-2-(4-(6-fluoropyridin-2-yl)benzyl)-5-methyl-3-(phenylamino)-2H-pyrazolo[3,4-d]pyrimidin-4(5H)-one 2-(4-(6-Fluoropyridin-2-yl)benzyl)-5-methyl-3-(phenylamino)-2H-pyrazolo[3,4-d]pyrimidine-4,6(5H,7H)-dione (1.42 g, 3.21 mmol) is suspended in POCl$_3$ (100 mL), and then slowly heated to reflux. After the mixture is refluxed overnight, POCl$_3$ is removed under reduced pressure. The obtained residue is dissolved in methylene chloride and then washed with saturated NaHCO$_3$ aqueous solution and brine successively. After the organic phase is evaporated to dryness, the obtained residue is purified on a silica gel column eluted with a gradient of 0-100% ethyl acetate in hexanes to give 957 mg of product (65% yield). MS (ESI) m/z 461.2 [M+H]$^+$.

(b) 2-(4-(6-Fluoropyridin-2-yl)benzyl)-6-hydrazinyl-5-methyl-3-(phenylamino)-2H-pyrazolo[3,4-d]pyrimidin-4(5H)-one A mixture of 6-chloro-2-(4-(6-fluoropyridin-2-yl)benzyl)-5-methyl-3-(phenylamino)-2H-pyrazolo[3,4-d]pyrimidin-4(5H)-one (180 mg, 0.39 mmol), hydrazine monohydrate (37 μL, 0.78 mmol) and DIPEA (135 μL, 0.78 mmol) in dioxane (6 mL) in a sealed vial is heated in a microwave reactor at 100° C. for 2 h. After cooled to room temperature, the mixture is evaporated to dryness. The residue is purified with a semi-preparative HPLC system equipped with a reversed-phase C18 column using a gradient of 0-60% acetonitrile in water containing 0.1% formic acid over 16 min to give 12 mg of product as a pale yellow solid. MS (ESI) m/z 457.2 [M+H]+.

(c) 8-Ethyl-2-(4-(6-fluoro-pyridin-2-yl)-benzyl)-5-methyl-3-phenylamino-2H,5H-pyrazolo[4,3-e][1,2,4]triazolo[4,3-a]pyrimidin-4-one To a solution of 2-(4-(6-fluoropyridin-2-yl)benzyl)-6-hydrazinyl-5-methyl-3-(phenylamino)-2H-pyrazolo[3,4-d]pyrimidin-4(5H)-one (11 mg, 0.024 mmol) in DMF (1 mL)

was added triethyl orthopropionate (5 drops). The reaction mixture is stirred at room temperature overnight. After the filtration, the filtrate is purified with a semi-preparative HPLC system equipped with a reversed-phase C18 column using a gradient of 0-80% acetonitrile in water containing 0.1% formic acid over 16 min to give 6.8 mg of product as an off-white solid (58% yield). MS (ESI) m/z 495.3 [M+H]+.

Example 2

2-(4-(6-Fluoro-pyridin-2-yl)-benzyl)-5,8-dimethyl-3-phenylamino-2H,5H-pyrazolo[4,3-e][1,2,4]triazolo[4,3-a]pyrimidin-4-one

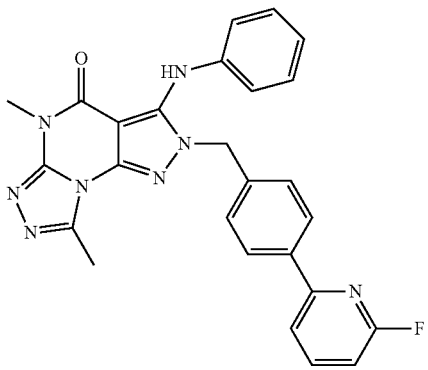 [SMILES: Cc1nnc2n(C)c(=O)c3c(Nc4ccccc4)n(Cc4ccc(-c5cccc(F)n5)cc4)nc3n12]

The compound is synthesized using a procedure similar to the one described in Example 1 wherein triethyl orthoacetate is added in step (c) instead of triethyl orthopropionate. Final product is obtained as an off white solid (HPLC purity: 98%). MS (ESI) m/z 481.2 [M+H]+.

Example 3

2-(4-(6-Fluoro-pyridin-2-yl)-benzyl)-5-methyl-3-phenylamino-2H,5H-pyrazolo[4,3-e][1,2,4]triazolo[4,3-a]pyrimidin-4-one

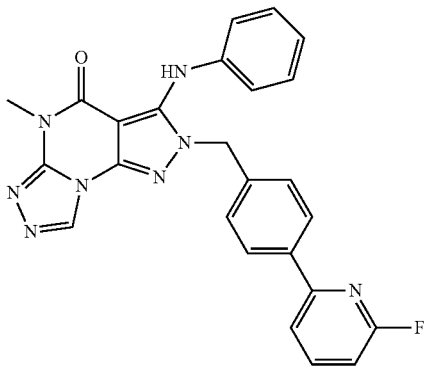 [SMILES: Cn1c(=O)c2c(Nc3ccccc3)n(Cc3ccc(-c4cccc(F)n4)cc3)nc2n2cnnc12]

The compound is synthesized using a procedure similar to the one described in Example 1 wherein triethyl orthoformate is added in step (c) instead of triethyl orthopropionate. Final product is obtained as an off white solid (HPLC purity: 96%). MS (ESI) m/z 467.2 [M+H]+.

Example 4

2-(4-bromo-benzyl)-5,8-dimethyl-3-phenylamino-2H,5H-pyrazolo[4,3-e][1,2,4]triazolo[4,3-a]pyrimidin-4-one

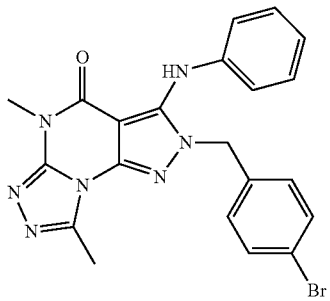 [SMILES: Cc1nnc2n(C)c(=O)c3c(Nc4ccccc4)n(Cc4ccc(Br)cc4)nc3n12]

The compound is synthesized using a procedure similar to the one described in Example 1 wherein 2-(4-bromobenzyl)-5-methyl-3-(phenylamino)-2H-pyrazolo[3,4-d]pyrimidine-4,6(5H,7H)-dione is used in step (a) instead of 2-(4-(6-fluoropyridin-2-yl)benzyl)-5-methyl-3-(phenylamino)-2H-pyrazolo[3,4-d]pyrimidine-4,6(5H,7H)-dione, and triethyl orthoacetate is added in step (c) instead of triethyl orthopropionate. Final product is obtained as a yellowish white solid (HPLC purity: 98%). MS (ESI) m/z 464 [M+H]+.

Example 5

2-(4-Acetylbenzyl)-5,8-dimethyl-3-(4-fluorophenylamino)-2H,5H-pyrazolo[4,3-e][1,2,4]triazolo[4,3-a]pyrimidin-4-one

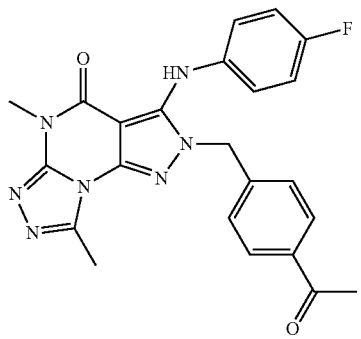 [SMILES: CC(=O)c1ccc(Cn2nc3c(c2Nc2ccc(F)cc2)c(=O)n(C)c2nnc(C)n32)cc1]

(a) 2-(4-Bromo-benzyl)-5,8-dimethyl-2H,5H-pyrazolo[4,3-e][1,2,4]triazolo[4,3-a]pyrimidin-4-one A The compound is synthesized using a procedure similar to the one described in Example 1 wherein 2-(4-bromobenzyl)-5-methyl-2H-pyrazolo[3,4-d]pyrimidine-4,6(5H,7H)-dione is used in step (a) instead of 2-(4-(6-fluoropyridin-2-yl)benzyl)-5-methyl-3-(phenylamino)-2H-pyrazolo[3,4-d]pyrimidine-4,6(5H,7H)-dione, and triethyl orthoacetate is added in step (c) instead of triethyl orthopropionate. Final product is obtained as an off-white solid (HPLC purity: 99%). MS (ESI) m/z 373.0 [M+H]+.

(b) 2-(4-Bromo-benzyl)-5,8-dimethyl-3-chloro-2H,5H-pyrazolo[4,3-e][1,2,4]triazolo[4,3-a]pyrimidin-4-one To a solution of 2-(4-bromo-benzyl)-5,8-dimethyl-3-phenylamino-2H,5H-pyrazolo[4,3-e][1,2,4]triazolo[4,3-a]pyrimidin-4-one (510 mg, 1.36 mmol) and hexachloroethane (1.94 g, 8.2 mmol) in $CH_2Cl_2$ (8 mL) is added 1.0 M LiHMDS in THF (2.2 mL, 2.2 mmol) dropwise. After the completion of the addition, the mixture is stirred at room temperature for 30 min and then diluted with $CH_2Cl_2$ (50 mL), followed by washing with saturated $NaHCO_3$ aqueous solution and brine. The organic phase is evaporated to dryness and the residue is purified on a silica gel column eluted with a gradient of 0% to 20% methanol in $CH_2Cl_2$ to give 497 mg of product as an off-white solid (89% yield). MS (ESI) m/z 407.0 [M+H]+.

(c) 5,8-Dimethyl-3-chloro-2H,5H-pyrazolo[4,3-e][1,2,4]triazolo[4,3-a]pyrimidin-4-one A mixture of 2-(4-bromo-benzyl)-5,8-dimethyl-3-chloro-2H,5H -pyrazolo[4,3-e][1,2,4]triazolo[4,3-a]pyrimidin-4-one (407 mg, 1.0 mmol) in trifluoroacetic acid (4 mL), trifluoromethanesulfonic acid (4 mL) and $CH_2Cl_2$ (8 mL) in a sealed vial is heated at 100° C. in a microwave reactor for an hour. The mixture is diluted with $CH_2Cl_2$ (40 mL) and then evaporated under reduced pressure. The residue is treated with $CH_2Cl_2$ (100 mL), cooled to −20° C. and then adjusted to pH 7-8 with $NaHCO_3$ powder. After filtration, the filtrate is washed with 10% methanol in $CH_2Cl_2$. The combined filtrate is evaporated to dryness. The obtained residue is purified with a small (12 g) silica gel cartridge eluted with a gradient of 0% to 20% methanol in $CH_2Cl_2$ to give 222 mg of product as a yellowish solid (93% yield). MS (ESI) m/z 239.0 [M+H]+.

(d) 2-(4-acetylbenzyl)-5,8-dimethyl-3-chloro-2H,5H-pyrazolo[4,3-e][1,2,4]triazolo[4,3-a]pyrimidin-4-one A mixture of 5,8-dimethyl-3-chloro-2H,5H-pyrazolo[4,3-e][1,2,4]triazolo[4,3-a]pyrimidin-4-one (48 mg, 0.20 mmol), 1-(4-(bromomethyl)phenyl)ethanone (43 mg, 0.20 mmol) and potassium carbonate (110 mg, 0.80 mmol) in DMF (1 mL) is stirred at room temperature for 2h. After filtration, the filtrate is evaporated to dryness. The residue is purified with a neutral aluminum oxide column eluted with a gradient of 0% to 8% methanol in CH2Cl2 to give 21.2 mg of product as an off-white solid (28% yield). MS (ESI) m/z 371.1 [M+H]+.

(e) 2-(4-Acetylbenzyl)-5,8-dimethyl-3-(4-fluorophenylamino)-2H,5H-pyrazolo[4,3-e][1,2,4]triazolo[4,3-a]pyrimidin-4-one A suspension of 2-(4-acetylbenzyl)-5,8-dimethyl-3-chloro-2H,5H -pyrazolo[4,3-e][1,2,4]triazolo[4,3-a]pyrimidin-4-one (28 mg, 0.076 mmol), 4-fluorobenzenamine (22 µL, 0.23 mmol) and potassium carbonate (32 mg, 0.23 mmol) in tert-amyl alcohol (1.0 mL) is degassed with argon and then Xantphos (5 mg, 0.0086 mmol) and $Pd_2(dba)_3$ (4 mg, 0.0043 mmol) are added. The suspension is degassed again and then heated at 110° C. for 18 h. After cooled to room temperature, the mixture is diluted with DMF and then filtered with a microfilter. The filtrate is purified with a semi-preparative HPLC system using a gradient of 0-45% acetonitrile in water containing 0.1% formic acid over 16 min to give 21.1 mg of the final product as an off white solid (HPLC purity: 96%; Yield: 63%). MS (ESI) m/z 446.2 [M+H]+.

Example 6

2-(4-methylbenzyl)-5,8-dimethyl-3-(4-fluorophenylamino)-2H,5H-pyrazolo[4,3-e][1,2,4]triazolo[4,3-a]pyrimidin-4-one

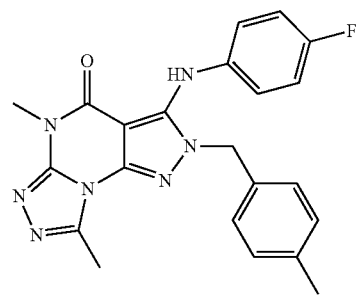 [SMILES: Cc1ccc(Cn2nc3c(c2Nc2ccc(F)cc2)c(=O)n(C)c2nnc(C)n32)cc1]

The compound is synthesized using a procedure similar to the one described in Example 5 wherein 1-(bromomethyl)-4-methylbenzene is used in step (d) instead of 1-(4-(bromomethyl)phenyl)ethanone. Final product is obtained as an off-white solid (HPLC purity: 98%). MS (ESI) m/z 418.2 [M+H]+.

Example 7

2-(4-(Pyridin-2-yl)-benzyl)-5,8-dimethyl-3-(4-fluorophenylamino)-2H,5H-pyrazolo[4,3-e][1,2,4]triazolo[4,3-a]pyrimidin-4-one

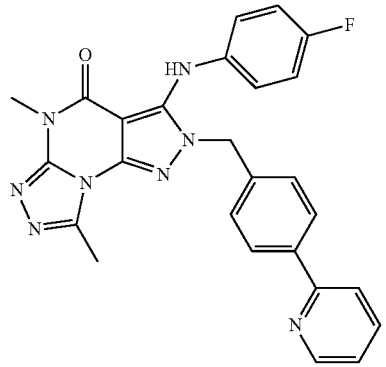 [SMILES: Cc1nnc2n(C)c(=O)c3c(Nc4ccc(F)cc4)n(Cc4ccc(-c5ccccn5)cc4)nc3n12]

A The compound is synthesized using a procedure similar to the one described in Example 5 wherein 2-(4-(bromomethyl)phenyl)pyridine is used in step (d) instead of 1-(4-(bromomethyl)phenyl)ethanone. Final product is obtained as an off-white solid (HPLC purity: 97%). 1H NMR (500 MHz, Chloroform-d) δ 8.73 (s, 1H), 8.01-7.65 (m, 4H), 7.43-7.27 (m, 1H), 7.15-6.89 (m, 7H), 5.03 (s, 2H), 3.64 (s, 3H), 2.83 (s, 3H). MS (ESI) m/z 481.2 [M+H]+.

Example 8

Measurement of PDEI Inhibition In Vitro Using IMAP Phosphodiesterase Assay Kit Phosphodiesterase 1 (including PDE1A, PDE1B and PDE1C) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization ($\Delta$mp). Inhibition of phosphodiesterase, therefore, is detected as a decrease in $\Delta$mp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: Phosphodiesterase enzymes that may be used include: 3',5'-cyclic-nucleotide -specific bovine brain phosphodiesterase (Sigma, St. Louis, Mo.) (predominantly PDE1B but also contains PDE1A and PDE1C) and recombinant full length human PDE1A, PDE1B and PDE1C which may be produced e.g., in HEK or SF9 cells by one skilled in the art. The PDE1 enzyme is reconstituted with 50% glycerol to 2.5 U/ml. One unit of enzyme will hydrolyze 1.0 µmol of 3',5'-cAMP to 5'-AMP per min at pH 7.5 at 30° C. One part enzyme is added to 1999 parts reaction buffer (30 µM, $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 µl of diluted enzyme solution is added into each well in a flat bottom 96-well polystyrene plate to which 1 µl of test compound dissolved in 100% DMSO is added. The compounds are mixed and pre-incubated with the enzyme for 10 min at room temperature. The FL-GMP conversion reaction is initiated by combining 4 parts enzyme and inhibitor mix with 1 part substrate solution (0.225 µM) in a 384-well microtiter plate. The reaction is incubated in dark at room temperature for 15 min. The reaction is halted by addition of 60 µl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization ($\Delta$mp).

A decrease in GMP concentration, measured as decreased $\Delta$mp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus $\Delta$mp, which allows $IC_{50}$ values to be estimated using nonlinear regression software (XLFit; IDBS, Cambridge, Mass.).

The Compounds of the Invention are tested in an assay as described or similarly described herein for PDE1 inhibitory activity, which compounds generally have $IC_{50}$ values against bovine PDE1 of less than 50 nM, and/or against PDE1A (HEK) of less than 25 nM.

Example 9

Pharmacokinetic Analysis of the Compounds of the Invention

Animals: Male, C57 BL/6 mice (Jackson Labs, 25-30 g in body weight) are provided by Jackson Laboratories. Up to five mice are housed per cage and are maintained under a 12 hour light/dark cycle with access to food and water ad libitum. All procedures for the handling and use of animals follow the guidelines of the Institutional Animal Care and Use Committee (IACUC) of Columbia University, in accordance with NIH guidelines. Eight week-old mice (N=3/dose level or treatment group) are used in the experiments.

Experimental Treatment: Compounds: Selected Compounds of the Invention are evaluated in the present study. Formulation/Vehicle: 3% 1N HCl, 5% Labrasol and 92% of 5% TPGS in 0.05M Citrate buffer (CB, pH 4.0). The test compound(s) are prepared as solution in vehicle and are dosed in a volume of 8 ml/kg.

Compound Preparation: Powdered stocks of the test compound(s) are measured and dissolved in 3% 1N HCl, 5% Labrasol and 92% of 5% TPGS in 0.05M Citrate buffer (CB, pH 4.0). Two or three layers of 3 mm glass beads are added to the bottom of the 10 ml glass tube to promote mixing. The tube is mixed using a benchtop vortex mixer then sonicated using a VWR sonicator (model 750) for about 5 min until the drug powder is totally dissolved in into a vehicle solution.

Treatment of Animals: Mice (N=3 mice/dose/time point) receive a 10 mg/kg oral (PO) dose of the test compound(s) at time 0. Groups of mice are killed at a specified time point, either 0.25, 0.5, 1, or 2 h after drug administration. Brain tissue is collected and frozen at −80° C., until analysis. Blood is collected from the mice by puncture of the retroorbital vein using a Pasteur pipette (VWR, Cat#53283-911), then deposited into silicon-coated blood collection tubes containing 0.105M sodium citrate solution (BD Vacutainer, #366392, Franklin Lakes, N.J.). Blood samples are centrifuged at the speed of 8000 g for 40 minutes in 4° C. (TOMY, refrigerated benchtop microcentrifuge, Fremont, Calif. 94583) and plasma decanted into Eppendorf tubes and frozen at −80° C. until analysis. Plasma and brain tissue samples are processed and analyzed by the analytical group using LC-MS/MS methods, as described below.

Sample Preparation: Samples of plasma are prepared for analysis as follows: 50 µL of the plasma samples is transferred into a 500 µl polypropylene microtube (Eppendorf Cat#022363611) as follows:

| Standards | Samples |
|---|---|
| 50 µL control (blank) plasma | 50 µL test sample plasma |
| 10 µL standard working solution in 1:1 Methanol:Water | 10 µL 1:1 Methanol:Water |
| 150 µL 0.1 µM Standard in Methanol | 150 µL 0.1 µM Standard in Methanol |

Each tube is vortex mixed, then centrifuged for 20 min at 15000 rpm. The supernatant is collected and 100 μL of each is then transferred into a 96-well polypropylene Elisa plate for mass spectrometric analysis.

Samples of brain homogenate were prepared for analysis as follows: Approximately 0.5 g of brain tissue is weighed and homogenized with 1 mL Milli-Q water. Then 60 μL of the resulting homogenate is then transferred into a clean 500 μL polypropylene microtube (Eppendorf Cat#022363611) and treated as shown below:

| Standards | Samples |
|---|---|
| 60 μL control (blank) brain homogenate | 60 μL test sample brain homogenate |
| 20 μL standard working solution in 1:1 Methanol:Water | 20 μL 1:1 Methanol:Water |
| 180 μL 0.1 μM Standard in Methanol | 180 μL 0.1 μM Standard in Methanol |

Each tube is vortexed, then centrifuged for 20 min at 15000 rpm using a Tomy benchtop centrifuge at 4° C. Standard is an internal standard used for LC-MS/MS quantitation. 150 μL, of each supernatant is then transferred into a 96-well plate for mass spectrometric analysis. Any remaining plasma or homogenate is stored at approximately −20° C. pending any necessary repeat analysis. For each test sample, a calibration curve is prepared covering the range of 0.5-500 ng/mL.

HPLC and Mass Spectrometric Analysis: Analysis to quantify the concentration of each compound in plasma and brain homogenate is carried out using reverse phase HPLC followed by mass spectrometric detection using the parameters listed:
HPLC: Waters Alliance 2795 HT
  Mobile phase A: 0.1% Formic acid in water
  Mobile phase B: 0.1% Formic acid in methanol
  Column: Phenomenex Synergi 4μ A Fusion-RP 50×2 mm
  Column Temperature: 40° C.

| Time (min) | Solvent A (%) | Solvent B (%) | Flow Rate (mL/min) |
|---|---|---|---|
| 0 | 80 | 20 | 0.6 |
| 2 | 0 | 100 | 0.6 |
| 4 | 0 | 100 | 0.6 |

Waters Alliance 2795 LC rapid equilibration flow (mL/min): 5
Waters Alliance 2795 LC rapid equilibration time (min): 0.25
  Re-equilibration time (min): 1
  Injection volume (μl): 10
Each compound is detected and quantified using Multiple Reaction Monitoring (MRM) of positive electrospray mode with a Waters QuattroMicro™ mass spectrometry system.

RESULTS: Plasma and Brain Analysis: All the test compound(s) tested could be detected and analyzed when spiked into control plasma. Standard curves are established prior to the analysis of the samples and proved linear over the range of 0.5-1500 ng/mL in plasma and 0.5-500 ng/mL in brain. Plasma and brain levels of each compound are determined and expressed as means±standard deviation for each compound at each time point. Brain and plasma $C_{max}$ and $T_{max}$ values are estimated for each compound by visual inspection of the data. A ratio of brain/plasma concentration (B/P) is also calculated for each compound by dividing Brain $AUC_{(0-2h)}$/Plasma $AUC_{(0-2h)}$.

Results: Using the procedure described or similarly described, the compounds of Examples 2 is tested and display oral bioavailability with low brain exposure (B/P ratio approximately 0.15 or below).

What is claimed is:
1. A compound of Formula I:

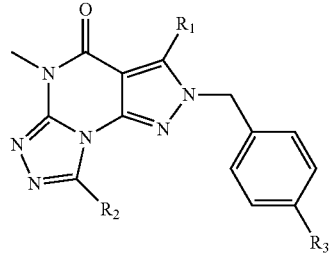

Formula I in free or salt form, wherein
(i) $R_1$ is —NH($R_2$), wherein $R_2$ is phenyl optionally substituted with halo;
(ii) $R_2$ is H or $C_{1-6}$alkyl;
(iii) $R_3$ is H, halogen, $C_{1-6}$alkyl, aryl optionally substituted with halogen, heteroaryl optionally substituted with halogen, or acyl.

2. The compound according to claim 1, wherein $R_1$ is —NH($R_2$), and wherein $R_2$ is phenyl.
3. The compound according to claim 1, wherein $R_1$ is —NH($R_2$), and wherein $R_2$ is 4-fluorophenyl.
4. The compound according to claim 1, wherein $R_2$ is $C_{1-6}$alkyl.
5. The compound according to claim 1, wherein $R_2$ is methyl.
6. The compound according to claim 1, wherein $R_2$ is ethyl.
7. The compound according to claim 1, wherein $R_2$ is H.
8. The compound according to claim 1, wherein $R_3$ is halogen.
9. The compound according to claim 1, wherein $R_3$ is heteroaryl optionally substituted with halogen.
10. The compound according to claim 1, wherein $R_3$ is pyrid-2-yl.
11. The compound according to claim 1, wherein $R_3$ is 6-fluoropyrid-2-yl.
12. The compound according to claim 1, wherein $R_3$ is acyl.
13. The compound according to claim 1 which is the compound:

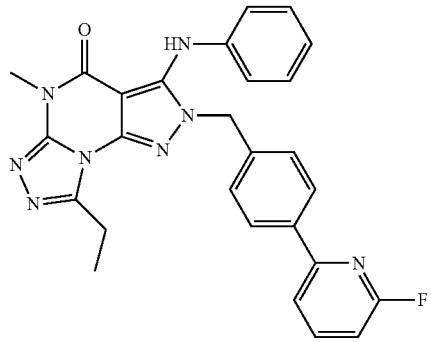 [SMILES: CCc1nnc2n(C)c(=O)c3c(Nc4ccccc4)n(Cc4ccc(-c5cccc(F)n5)cc4)nc3n12]

in free or salt form.

14. The compound according to claim 1 which is the compound:

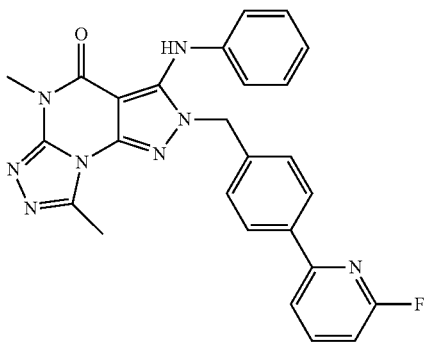 [SMILES: Cc1nnc2n(C)c(=O)c3c(Nc4ccccc4)n(Cc4ccc(-c5cccc(F)n5)cc4)nc3n12]

in free or salt form.

15. The compound according to claim 1 which is the compound:

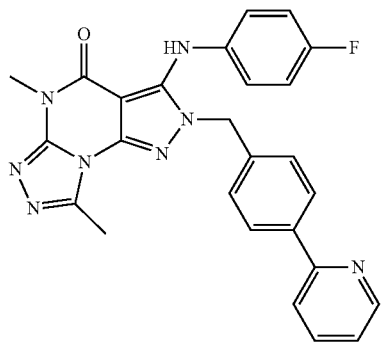 [SMILES: Cc1nnc2n(C)c(=O)c3c(Nc4ccc(F)cc4)n(Cc4ccc(-c5ccccn5)cc4)nc3n12]

in free or salt form.

16. The compound according to claim 1 which is the compound:

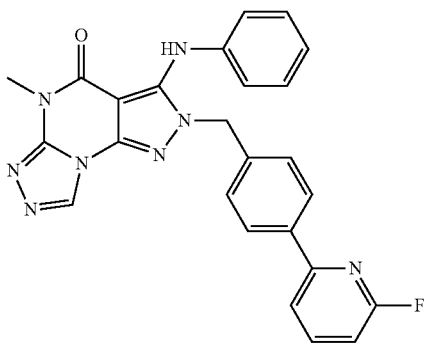 [SMILES: Cn1c(=O)c2c(Nc3ccccc3)n(Cc3ccc(-c4cccc(F)n4)cc3)nc2n2cnnc12]

in free or salt form.

17. A combination comprising the compound according to claim 1, in free or pharmaceutically acceptable salt form, and one or more other therapeutic agents useful for the treatment of cardiovascular disorders, in free or pharmaceutically acceptable salt form.

18. A pharmaceutical composition comprising the compound according to claim 1, in free or pharmaceutically acceptable salt form.

19. A method for the treatment of a disease or disorder which may be ameliorated by modulating cGMP/PKG-dependent signaling pathways comprising administering to a patient in need thereof an effective amount of the compound according to claim 1, in free or pharmaceutically acceptable salt form.

20. The method according to claim 19, wherein the disease or disorder is a cardiovascular disorder.

21. The method according to claim 20 wherein the disease or disorder is selected from the group consisting of: hypertrophy, atherosclerosis, myocardial infarction, congestive heart failure, angina, hypertension, essential hypertension, pulmonary hypertension, pulmonary arterial hypertension, secondary pulmonary hypertension, isolated systolic hypertension, hypertension associated with diabetes, hypertension associated with atherosclerosis, and renovascular hypertension.

22. The method according to claim 21, wherein the disease or disorder is cardiac hypertrophy.

23. The method according to claim 19, further comprising administering a PDE5 inhibitor, in free or pharmaceutically acceptable salt form.

24. The method according to claim 19, wherein the disease or disorder is a stroke.

25. The method according to claim 24, wherein the stroke is characterized as a transient ischemic attack.

26. The method according to claim 19, wherein the disease or disorder is a cardiovascular disease or disorder that is associated with a muscular dystrophy.

27. The method according to claim 26, wherein the disease or disorder is a cardiovascular dysfunction which results from a muscular dystrophy selected from the group consisting of: Duchenne muscular dystrophy, Becker muscular dystrophy, limb-girdle muscular dystrophy, myotonic dystrophy, and Emery-Dreifuss muscular dystrophy.

28. The method according to claim 19, wherein the disease or disorder is selected from the group consisting of: renal failure, fibrosis, an inflammatory disease or disorder, vascular remodeling, and a connective tissue disease or disorder.

29. A pharmaceutical composition comprising the combination according to claim 17, in admixture with a pharmaceutically acceptable diluent or carrier.

30. A method for the treatment of a disease or disorder which may be ameliorated by modulating cGMP/PKG-dependent signaling pathways comprising administering to a patient in need thereof an effective amount of the combination according to claim 17.

* * * * *